United States Patent [19]

Rivier et al.

[11] Patent Number: 4,489,061

[45] Date of Patent: * Dec. 18, 1984

[54] TREATMENT OF MALE MAMMALS

[75] Inventors: Catherine L. Rivier; Jean E. F. Rivier; Wylie W. Vale, Jr., all of La Jolla, Calif.

[73] Assignee: The Salk Institute for Biological Studies, San Diego, Calif.

[*] Notice: The portion of the term of this patent subsequent to Mar. 22, 2000 has been disclaimed.

[21] Appl. No.: 423,734

[22] Filed: Sep. 27, 1982

Related U.S. Application Data

[63] Continuation of Ser. No. 272,968, Jun. 12, 1981, Pat. No. 4,377,574.

[51] Int. Cl.$^3$ ............................................. A61K 37/00
[52] U.S. Cl. .................................................... 424/177
[58] Field of Search ........................................ 424/177

[56] References Cited

U.S. PATENT DOCUMENTS 4,377,574 3/1983 Rivier et al. ............. 260/112.5 LH

OTHER PUBLICATIONS

Bowers, et al., Biochem. & Biophys. Res. Commun. 72, (1976) 1003–1007.
C. Rivier, et al., Endocrinology 108, (1981) 1998–2001.
Chem. Abstr. 94, (1981) 25238n, 41612k, 41539s.
Chem. Abstr. 95, (1981) 91232c.
Chem. Abstr. 89, (1978) 157886d.
R. Lind, et al., Reversible Inhibition of Spermatogenesis 305, 663–667.
Science 210, (1980) 93,94.
Acta Endocrinologica 91, (1979) 601–608.

*Primary Examiner*—Delbert R. Phillips
*Attorney, Agent, or Firm*—Fitch, Even, Tabin & Flannery

[57] ABSTRACT

Peptides which are LRF analogs that inhibit the secretion of gonadotropins by the pituitary gland and inhibit the release of steroids by the gonads can be effective to suppress androgen-dependent behavior when administered to male mammals. The peptides are LRF antagonists having a binding affinity at least about 15 times that exhibited by LRF and having an $ICR_{50}$ of less than 1/1. Examples of peptides which may be used are those having the structure:

$R_1$-$R_2$-$R_3$-D-Trp-Ser-Tyr-$R_4$-Leu-Arg-Pro-Gly-$NH_2$ wherein $R_1$ is selected from the group consisting of hydrogen, formyl, acetyl, acrylyl, benzoyl and allyl; $R_2$ is selected from the group consisting of dehydro Pro, dehydro D-Pro, Thz and D-Thz; $R_3$ is selected from the group consisting of pCl-D-Phe, pF-D-Phe, $pNO_2$-D-Phe and 3,4 Cl-D-Phe; $R_4$ is selected from the group consisting of D-Trp and (imBzl) D-His; and Leu may be substituted by NαMeLeu.

Effective suppression of androgen-dependent behavior is achieved at a daily dosage level of not more than about 3 mg. per Kg. of body weight.

10 Claims, No Drawings

TREATMENT OF MALE MAMMALS

This invention was made with Government support under NIH Grant HD-09690 awarded by DHHS. The Government has certain rights in this invention.

This application is a continuation of U.S. Ser. No. 272,968, filed June 12, 1981 now U.S. Pat. No. 4,377,574, which claimed priority from International Appn. No. PCT/US80/00818 filed June 26, 1980 under 35 USC 363, as a continuation-in-part thereof, as provided for in 35 USC 365(c).

The present invention relates to peptides which inhibit the release of gonadotropins by the pituitary gland in mammalians, including humans, and more specifically to methods of suppressing androgen-dependent behavior by administering to male mammals such peptides which inhibit gonadal function and the release of the steroidal hormones, progesterone and testosterone.

BACKGROUND OF THE INVENTION

The pituitary gland is attached by a stalk to the region in the base of the brain known as the hypothalamus. The pituitary gland has two lobes, the anterior and the posterior lobes. The posterior lobe of the pituitary gland stores and passes onto the general circulation two hormones manufactured in the hypothalamus, these being vasopressin and oxytocin. The anterior lobe of the pituitary gland secretes a number of hormones, which are complex protein or glyco-protein molecules that travel through the bloodstream to various organs and which, in turn, stimulate the secretion into the bloodstream of other hormones from the peripheral organs. In particular, follicle stimulating hormone(FSH) and luteinizing hormone(LH), sometimes referred to as gonadotropins or gonadotropic hormones, are released by the pituitary gland. These hormones, in combination, regulate the functioning of the gonads to produce testosterone in the testes and progesterone and estrogen in the ovaries, and also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH. The hypothalamic hormone which acts as a releasing factor for LH is referred to herein as LRF although it has also been referred to as LH-RH and as GnRH. LRF has been isolated and characterized as a decapeptide having the following structure:

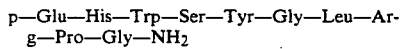

Peptides are compounds which contain two or more amino acids in which the carboxyl group of one acid is linked to the amino group of the other acid. The formula for LRF, as represented above, is in accordance with conventional representation of peptides where the amino group appears to the left and the carboxyl group to the right. The position of the amino acid residue is identified by numbering the amino acid residues from left to right. In the case of LRF, the hydroxyl portion of the carboxyl group of glycine has been replaced with an amino group (NH$_2$). The abbreviations for the individual amino acid residues above are conventional and are based on the trivial name of the amino acid: where p-Glu is pyroglutamic acid, His is histidine, Trp is tryptophan, Ser is serine, Tyr is tyrosine, Gly is glycine, Leu is Leucine, Arg is arginine and Pro is proline. Except for glycine, amino acids of the peptides of the invention are of the L-configuration unless noted otherwise.

It is known that the substitution of D-amino acids for Gly in the 6-position of the LRF decapeptide can provide a peptide material having from about 1 to 35 times greater potency, relative to LRF, to effect the release of LH and other gonadotropins by the pituitary gland of mammalians. The releasing effect is obtained when the LRF analog, referred to as an LRF agonist, is introduced into the bloodstream of a mammalian.

It is also known that substitution of various amino acids for His (or the deletion of His) at the 2-position of the LRF decapeptide can produce analogs, referred to as LRF antagonists, having an inhibitory effect on the release of LH and other gonadotropins by the pituitary gland of mammalians. In particular, varying degrees of inhibition of the release of LH are obtained when His is deleted (des His) or replaced by D-Ala, D-Phe or Gly. The inhibitory effect of such peptides modified at the 2-position can be further enhanced when a D-amino acid is substituted for Gly in the 6-position of the decapeptides. For example, the peptide: [des His$^2$, D-Ala$^6$]-LRF, i.e., pGlu—Trp—Ser—Tyr—D—Ala—Leu—Arg—Pro—Gly—NH$_2$, is 3 times more potent as an inhibitor for the release of gonadotropins than is the same peptide where Gly is present in the 6-position rather than D-Ala.

Some female mammalians who have no ovulatory cycle and who show no pituitary or ovarian defect begin to secrete normal amounts of the gonadotropins LH and FSH after the appropriate administration of LRF. Thus, the administration of LRF is considered suitable for the treatment of those cases of infertility where a functional defect resides in the hypothalamus. There are also reasons for desiring to prevent ovulation in female mammalians, and the administration of LRF antagonists have been used to prevent ovulation. It has also been found that the administration of potent agonists have exhibited potential use as a contraceptive by substantially decreasing the sperm count in male mammals; however, more effective methods of contraception for male mammals using LRF analogs were sought.

SUMMARY OF THE INVENTION

The present invention provides a method for treatment of male mammals, including humans, to suppress androgen-dependent behavior using peptides which strongly inhibit the release of gonadotropins. The administration of these LRF analogs that are strongly antagonistic to LRF has an inhibitory effect on the reproduction processes of male mammals and accomplishes both a suppression of androgen-dependent behavior and such a substantial decrease in the sperm count that fertilization is effectively prevented.

Generally, in accordance with the present invention, it has been found that the repeated administration of LRF antagonists, which strongly inhibit the secretion of gonadotropins by the pituitary gland of mammalians, including humans, and inhibit the release of steroids by the gonads, can be employed to suppress androgen-dependent behavior in males, particularly aggressiveness and desire to mate, because they are effective at low enough dosage levels, i.e., not more than about 3 milligrams per day per kilogram of body weight, to eliminate undersirable dermatological and other side effects Preferably the peptide has a binding affinity at least about 15 times that exhibited by LRF. The peptide should have an ICR50 of less than 1/1, and can be administered by any suitable and convenient method, such as orally, by injection or subcutaneously. Oral administration, is preferred for humans; however, injection may be preferable for veterinary uses. The peptide can be combined with suitable pharmaceutically acceptable carriers or dilluents, such as vegetable oil, sugars, corn starch, polysaccharides and gums. The peptide might be administered daily for 7 consecutive days out of each month. Alternatively, it might be administered each day at a somewhat lower level together with suitable androgens.

Such peptides are often administered in the form of pharmaceutically acceptable nontoxic salts, such as acid addition salts or metal complexes, e.g., with zinc, iron or the like (which are considered as addition salts for purposes of this application). Illustrative of such acid addition salts are hydrochloride, hydrobromide, sulphate, phosphate, maleate, acetate, citrate, benzoate, succinate, malate, ascorbate, tartrate and the like.

DESCRIPTION OF THE PREFERRED EMBODIMENTS

Exemplary of the peptides which may be used are LRF antagonists wherein there are substitutions in the 1- and 6-positions, wherein substituted D-Phe is present in the 2-position and wherein D-Trp is present in the 3-position. The 1-position may contain dehydro-Pro, dehydro-D-Pro, Thz or D-Thz. The 6-position may contain either D-Trp of (imBzl)D-His. Moreover, certain substitutions may optionally be made in the 7 and 10 positions. By dehydro Pro is meant 3,4 dehydroProline, $C_5H_7O_2N$, and when $R_1$ is an acyl radical, it is attached to the nitrogen. By Thz is meant meta-thiazolidine-2-carboxylic acid, $C_4H_7O_2NS$, which can be prepared by the treatment of cysteine hydrochloride with formaldehyde. When $R_1$ is an acyl radical, it is attached to the nitrogen; for example, Ac-Thz is prepared by the reaction of Thz with acetic anhydride.

More specifically, the peptides of the present invention are represented by the following formula:

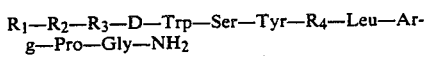

wherein $R_1$ is selected from the group consisting of hydrogen, formyl, acetyl, acrylyl, benzoyl and allyl; $R_2$ is selected from the group consisting of dehydro Pro, dehydro D-Pro, Thz and D-Thz; $R_3$ is selected from the group consisting of pCl—D—Phe, pF—D—Phe, pNO$_2$—D—Phe and 3,4 Cl—D—Phe; $R_4$ is selected from the group consisting of D-Trp and (imBzl)D-His. In addition, Leu may be substituted by NαMeLeu, and Gly-NH$_2$ may be substituted by NHCH$_2$CH$_3$ or some other alkyl amide having 1 to 5 carbon atoms. Other equivalent acyl groups can be used at $R_1$.

The peptides of the present invention can be synthesized by a solid phase technique using a chloromethylated resin for those peptides wherein an alkyl amide is present and a benzhydrylamine (BHA) resin for those peptides wherein Gly—NH$_2$ is present. The synthesis is conducted in a manner to stepwise add the amino acids in the chain in the manner set forth in detail in the U.S. Pat. No. 4,072,668, the disclosure of which is incorporated herein by reference. Side-chain protecting groups, as are well known in the art, are added to Ser, Tyr, Arg and His before these amino acids are coupled to the chain being built up upon the resin.

Such a method provides the fully protected intermediate peptidoresin. The fully protected peptide can be cleaved from the resin support by aminolysis, as is well known in the art, to yield the fully protected amide intermediate. The intermediates of the invention may be represented as:

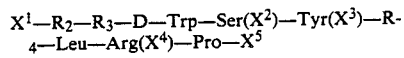

wherein: $X^1$ is an -amino protecting group of the type known to be useful in the art in the stepwise synthesis of polypeptides and when $R_1$ in the desired peptide composition is a particular acyl group, that group may be used as the protecting group. Among the classes of α-amino protecting groups covered by $X^1$ are (1) acyl-type protecting groups, such as formyl, trifluoroacetyl, phthalyl, Tos, benzoyl, benzensulfonyl, nitrophenylsulfenyl, tritylsulfenyl, o-nitrophenoxyacetyl, acrylyl, chloroacetyl, acetyl and γ-chlorobutyryl; (2) aromatic urethan-type protecting groups, e.g., benzyloxycarbonyl and substituted benzyloxycarbonyl, such as p-chloro-benzyloxycarbonyl, p-nitrobenzyloxycarbonyl, p-bromobenzyl-oxycarbonyl and p-methoxybenzyloxycarbonyl; (3) aliphatic urethan protecting groups, such as terbutyloxycarbonyl (Boc), diisopropylmethoxycarbonyl, isopropyloxycarbonyl, ethoxycarbonyl and alyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl, triphenylmethyl(trityl) and benzyl; (7) trialkylsilane groups, such as trimethylsilane. The preferred α-amino protecting group is Boc when $R_1$ is hydrogen $X^2$ is a protecting group for the alcoholic hydroxyl group of Ser and is selected from the group consisting of acetyl, benzoyl, tetrahydropyranyl, tert-butyl, trityl, benzyl and 2,6-dichlorobenzyl. Benzyl is preferred.

$X^3$ is a protecting group for the phenolic hydroxyl group of Tyr selected from the group consisting of tetrahydropyranyl, tert-butyl, trityl, benzyl, benzyloxycarbonyl, 4-bromobenzyloxycarbonyl and 2,6-dichlorobenzyl. 2,6-dichlorobenzyl is preferred.

$X^4$ is a protecting group for the guanidino group of Arg and is selected from the group consisting of nitro, Tos, benzyloxycarbonyl, adamantyloxycarbonyl, and Boc; alternatively $X^4$ may be hydrogen, which means there are no protecting groups on the side chain nitrogen atoms of arginine.

$X^5$ is selected from dimethylamine, alkylamine of 1 to 5 carbon atoms, phenethylamine, O-CH$_2$-[resin support] or Gly-O-CH$_2$-[resin support] or Gly-NH-[resin support].

The criterion for selecting side chain protecting groups for $X^2$-$X^4$ are that the protecting group must be stable to the reagent under the reaction conditions selected for removing the -amino protecting group at each step of the synthesis, the protecting group must not be split off under coupling conditions and the protecting group must be removable upon completion of the synthesis of the desired amino acid sequence under reaction conditions that will not alter the peptide chain.

When the $X^5$ group is -O-CH$_2$-[resin support] or Gly-O-CH$_2$-[resin support], the ester moiety of one of the many functional groups of the polystyrene resin support is being represented. When the $X^5$ group is Gly-NH-[resin support], an amide bond connects Gly to BHA resin or to a paramethyl BHA resin.

When $R_1$ is acetyl, formyl, acrylyl, benzoyl, or allyl, it may be employed as the $X^1$ protecting group for the α-amino group of proline or Thz, in which case it can be added to proline or to Thz before it is coupled with the peptide chain. Acetyl is abbreviated as Ac, and acrylyl is abbreviated as Acr. Alternatively, a reaction may be carried out with the peptide on the resin, e.g., reacting with acetic acid in the presence of dicyclohexyl carbodiimide (DCC) or with acetic anhydride.

Deprotection of the peptides as well as cleavage of the peptide from the benzhydrylamine resin takes place at 0° C. with hydrofluoric acid (HF). Anisole is added to the peptide prior to treatment with HF. After the removal of HF, under vacuum, the cleaved, deprotected peptide is treated with ether, decanted, taken in dilute acetic acid and lyophilized. Purification of the peptide is effected by ion exchange chromotography on a CMC column, followed by partition chromatography using the elution system: n-butanol; 0.1 N acetic acid (1:1 volume ratio) on a column packed with Sephadex G 25.

The peptides of the invention are considered to be effective at levels of 200 micrograms per kilogram of body weight. It is presently intended to use dosage levels in the range of from about 0.1 to about 3 milligrams per kilogram of body weight when these antagonists are administered to male mammals on a regular basis to suppress androgen-dependent behavior; however, it is not certain that body weight is true criterion so lesser amounts may be effective. Treatment less frequently than on a daily basis is also considered to be effective.

The following examples further illustrate various features of the invention but are intended to in no way limit the scope of the invention which is defined in the appended claims.

EXAMPLE I

For purposes of an example, a representative solid phase synthesis of [Ac-dehydro Pro$^1$, pCl—D—Phe$^2$, D—Trp$^{3,6}$, NαMeLeu$^7$]-LRF is set forth hereinafter. This peptide has the following formula:
Ac—dehydro Pro—pCl—D—Phe—D—Trp—Ser—Tyr—D—Trp—NαMeLeu—Arg—Pro—Gly—NH$_2$ A BHA resin is used, and Boc-protected Gly is coupled to the resin over a 2-hour period in CH$_2$Cl$_2$ using a 3-fold excess of Boc derivative and DCC as an activating reagent. The glycine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | CH$_2$Cl$_2$ wash - 80 ml. (2 times) | 3 |
| 2 | Methanol(MeOH) wash - 30 ml. (2 times) | 3 |
| 3 | CH$_2$Cl$_2$ wash - 80 ml. (3 times) | 3 |
| 4 | 50 percent TFA plus 5 percent 1,2-ethanedithiol in CH$_2$Cl$_2$ - 70 ml. (2 times) | 10 |
| 5 | CH$_2$Cl$_2$ wash - 80 ml. (2 times) | 3 |
| 6 | TEA 12.5 percent in CH$_2$Cl$_2$ - 70 ml. (2 times) | 5 |
| 7 | MeOH wash - 40 ml. (2 times) | 2 |
| 8 | CH$_2$Cl$_2$ wash - 80 ml. (3 times) | 3 |
| 9 | Boc-amino acid DMF or CH$_2$Cl$_2$, (10 mmoles) in 30 ml. of either depending upon the solubility of the particular protected amino acid, (1 time) plus DCC (10 mmoles) in CH$_2$Cl$_2$ | 30–300 |
| 10 | MeOH wash - 40 ml. (2 times) | 3 |
| 11 | TEA 12.5 percent in CH$_2$Cl$_2$ - 70 ml. (1 time) | 3 |
| 12 | MeOH wash - 30 ml. (2 times) | 3 |
| 13 | CH$_2$Cl$_2$ wash - 80 ml. (2 times) | 3 |

After step 13, an aliquot is taken for ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. NαBoc protection is used for each of the remaining amino acids throughout the synthesis. The side chain of Arg is protected with Tos. Bzl is used as a side chain protecting group for the hydroxyl group of Ser, and 2-6 dichlorobenzyl is used as the side chain protecting group for the hydroxyl group of Tyr. N—acetyl—dehydro Pro is introduced as the final amino acid. Boc—Arg(Tos) and Boc—D—Trp, which have low solubility in CH$_2$Cl$_2$, are coupled using DMF.

The cleavage of the peptide from the resin and complete deprotection of the side chains takes place very readily at 0° C. with HF. Anisole is added as a scavenger prior to HF treatment. After the removal of HF under vacuum, the resin is extracted with 50 volume % acetic acid, and the washings after dilution with H$_2$O to less than 10 volume % are lyophilized to provide a crude peptide powder.

Purification of the peptide is then effected by ion exchange chromatography on CMC (Whatman CM 32, using a step gradient of 0.12 M NH$_4$OAc in 50/50 methanol/water) followed by partition chromatography in a gel filtration column using the elution system: n-Butanol; 0.1 N Acetic acid (1:1-volume ratio).

The peptide is assayed in vitro using dissociated rat pituitary cells maintained in culture for 4 days prior to the assay. The levels of LH mediated in response to the application of peptides is assayed by specific radioimmunoassay for rat LH. Control dishes of cells receive LRF only (3 nanomolar). Experimental dishes receive a measure that is 3 nanomolar in LRF plus a measure having a concentration of test peptide ranging from 1 to 100 nanomolar. The amount of LH secreted in the samples treated only with LRF is compared with that secreted by the samples treated with the peptide plus LRF to determine the ratio at which an amount of the antagonist will inhibit the activity of a certain amount of LRF. Results are calculated and expressed as the molar concentration ratio of test peptide to LRF (antagonist/LRF) required to reduce the amount of LH released by 3 nanomolar LRF to 50 percent of the control value (ICR$_{50}$). For the peptide to be considered effective for use in the method of the present invention, it should have an ICR$_{50}$ of less than 1/1. The Example I peptide has an ICR$_{50}$ of 0.043/1 and a binding affinity about 25 times that of LRF.

The peptide is used at a level effective to reduce testes and seminal vesicles weights and also to inhibit spermatogenesis after a 14-day administration to male rats. Testosterone(T) levels of antagonist-treated male rats are comparable to those of control animals within one week following cessation of treatment for 14 days. Prostate weights of male rats recover in 2–3 weeks and seminal vesicles weights in 4–5 weeks. It is preferred to use dosage levels in the range of from about 0.1 to about 1 milligram per rat per day, which can be administered without detrimental side effects.

It may be possible to use lower levels of the antagonists or to administer them less frequently and still achieve similar results. For example, after administration of the antagonist has taken place for about 3–4 weeks, intermittent administration at a frequency of only once a week is considered sufficient to maintain disruption of spermatogenesis. Likewise daily administration is not considered necessary even during the initial period. Administration every other day of a dose of about 3 mg/Kg. of body weight of an antagonist having an ICR$_{50}$ of about 0.04 will effectively prevent fertilization after 4 injections, and following treatment for about 2 weeks, spermatogenesis is considered to have effectively ceased and androgen-dependent behavior has been suppressed.

EXAMPLE II

Male rats (about 320 grams each) are each treated with 1 milligram of the peptide synthesized in Example I, once a day, for 14 days by injection in 0.2 ml. of corn oil. All the rats show a decrease in testes and seminal vesicles weight, spermatogenesis and plasma androgen levels. Moreover, immunoreactive gonadotropin and steroid levels, i.e. LH, FSH, Testosterone and dihydrotestosterone (DHT) in the treated male animals were decreased relative to control animals.

The rats have no desire to mate and thus do not cause fertilization after treatment has progressed for about 7 consecutive days. Histological examination of the testes following the 14-day treatment reveals arrested spermatogenesis for a period of several weeks following cessation of the daily injections.

Full recovery of testes and seminal vesicle weights, androgen-dependent behavior and spermatogenesis ultimately occurs following cessation of the 14-day peptide administration. After about four weeks, the testes weights are equal to about 80% that of the control group and sexual behavior returns to normal, and about seven days thereafter good spermatogenesis is apparent in a majority of the tubules. Fertility, as assessed by the ability to impregnate females, is restored in all of the rats which have not been sacrificed within 6 weeks after cessation of the injections.

The peptide tested is useful for treatment to suppress androgen-dependent behavior in male mammals without harmful side effects or irreversible damage.

EXAMPLE III

Additional LRF antagonists having the general formula:

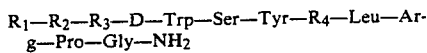

are synthesized as set forth below:

| Peptide | R$_1$ | R$_2$ | R$_3$ | R$_4$ |
|---------|-------|-------|-------|-------|
| A | Ac | dehydro Pro | pF—D-Phe | D-Trp |
| B | Acr | dehydro Pro | pCl—D-Phe | D-Trp |
| C | Ac | dehydro Pro | pCl—D-Phe | (imBzl)D-His |
| D | Ac | Thz | pCl—D-Phe | D-Trp |
| E | Ac | dehydro Pro | pCl—D-Phe | D-Trp |

These peptides are also tested in the manner set forth for the peptide of Example I and are found to have an (ICR$_{50}$) as set forth below.

| Peptide | (ICR$_{50}$) |
|---------|--------------|
| A | 0.06/1 |
| B | 0.04/1 |
| C | 0.10/1 |
| D | 0.15/1 |
| E | 0.04/1 |

These peptides are then tested in accordance with the procedure of Example II, and all five peptides are found useful to suppress androgen-dependent behavior when administered to male mammals at a similar dosage for similar time periods.

EXAMPLE IV

A first group (I) of male rats (about 320 grams each) are each treated with 1 milligram of Peptide A synthesized in Example III, every day for 14 days, by injection in 0.2 ml. of corn oil. All the rats show a decrease in testes and seminal vesicles weight, spermatogenesis and plasma androgen levels. Moreover, immunoreactive gonadotropin and steroid levels, i.e. LH, FSH, Testosterone and dihydrotestosterone (DHT) in the treated male animals were decreased relative to the control animals accounting for the suppression of androgen-dependent behavior.

A second group (II) of similar male rats is each similarly injected with this dosage of antagonist plus 0.2 mg. of testosterone propionate(TP). All of the rats in the second group maintain their androgen-dependent behavior, particularly their desire to mate, while the rats of the first group quickly lose their androgen-dependent behavior, including their desire to mate, and none causes fertilization after the fourth injection. However, the ability of the second group to sire offspring drops off quickly, and all of the rats are infertile at the end of the 2-week treatment period. Therefore, Group II remained sexually active but infertile, while Group I exhibited no active sexual behavior.

Periodic histological examination of the testes of rats from Group I following the 14-day treatment reveals arrested spermatogenesis for a period of a few weeks following cessation of the daily injections. Full recovery of testes and seminal vesicle weights as well as desire to mate and spermatogenesis occurs following cessation of the 2-week period of administration.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications in the other members of the LRF chain can be made in accordance with well-known developments that have created known, useful analogs of LRF. Moreover, other substitutions which do not significantly detract from the effectiveness of the peptides may be employed in peptides used in accordance with the invention, and equivalent acyl groups can be substituted for those mentioned for $R_1$.

Various features of the invention are emphasized in the claims which follow.

What is claimed is:

1. A method for suppressing aggressiveness and desire to mate in male mammals comprising administering an effective amount of a peptide or a nontoxic salt thereof to a male mammal, at a daily dosage level of not more than about 3 milligrams per kilogram of body weight, said peptide being an LRF antagonist having an $ICR_{50}$ of less than 1/1.

2. A method in accordance with claim 1 wherein said peptide has the formula:

$$R_1-R_2-R_3-D-Trp-Ser-Tyr-R_4-Leu-Arg-Pro-Gly-NH_2$$

wherein $R_1$ is selected from the group consisting of H, formyl, Ac, Acr, benzoyl and allyl; $R_2$ is selected from the group consisting of dehydro Pro, dehydro D-Pro, Thz and D-Thz; $R_3$ is selected from the group consisting of pCl—D—Phe, pF—D—Phe, pNO$_2$—D—Phe, and 3,4 Cl—D—Phe; $R_4$ is selected from the group consisting of D-Trp and (imBzl) D-His, and wherein Leu may be substituted by N$\alpha$Me-Leu and Gly-NH$_2$ by NHCH$_2$CH$_3$.

3. A method in accordance with claim 2 wherein $R_2$ is dehydro-Pro and $R_4$ is D-Trp.

4. A method in accordance with claim 2 wherein $R_4$ is (imBzl)D-His.

5. A method in accordance with either claim 3 or 4 wherein $R_3$ is pCl-D-Phe.

6. A method in accordance with claim 3 wherein $R_3$ is pF—D—Phe.

7. A method in accordance with claim 1 wherein said peptide has the formula:
Ac—dehydro Pro—pCl—D—Phe—D—Trp—Ser—Tyr—D—Trp—Leu—Arg—Pro—Gly—NH$_2$.

8. A method in accordance with claim 1 wherein said peptide has the formula:
Ac—dehydro Pro—pCl—D—Phe—D—Trp—Ser—Tyr—D—Trp—N$\alpha$MeLeu—Arg—Pro—Gly—NH$_2$.

9. A method in accordance with claim 1 wherein an effective amount is administered at least every other day for a period of at least about 2 weeks.

10. A method in accordance with claim 1 wherein the dosage administered is between 200 micrograms and about 3 milligrams per kilogram of body weight.

* * * * *